(12) United States Patent
Minehan et al.

(10) Patent No.: US 11,567,821 B2
(45) Date of Patent: Jan. 31, 2023

(54) HEALTH REPORTING FOR COMPUTING DEVICES

(71) Applicant: CORE SCIENTIFIC, INC., Bellevue, WA (US)

(72) Inventors: Kristy-Leigh Anne Minehan, Bellevue, WA (US); Ganesh Balakrishnan, Sammamish, WA (US); Evan Adams, Bainbridge Island, WA (US); Carla Cortez, Playa Del Rey, CA (US); Ian Ferreira, Issaquah, WA (US)

(73) Assignee: Core Scientific Operating Company, Bellevue, WA (US)

( * ) Notice: Subject to any disclaimer, the term of this patent is extended or adjusted under 35 U.S.C. 154(b) by 183 days.

(21) Appl. No.: 16/936,101

(22) Filed: Jul. 22, 2020

(65) Prior Publication Data

US 2021/0026727 A1    Jan. 28, 2021

Related U.S. Application Data

(60) Provisional application No. 62/877,740, filed on Jul. 23, 2019, provisional application No. 62/877,719, filed on Jul. 23, 2019.

(51) Int. Cl.
    *G06F 11/07*     (2006.01)
    *G01N 33/00*     (2006.01)
    (Continued)

(52) U.S. Cl.
    CPC .......... *G06F 11/0775* (2013.01); *G01K 3/005* (2013.01); *G01N 33/0063* (2013.01);
    (Continued)

(58) Field of Classification Search
    CPC .. G06F 11/0775; G06F 11/0751; G06F 11/30; G01K 3/005; G01N 33/0063
    (Continued)

(56) References Cited

U.S. PATENT DOCUMENTS 5,956,665 A  *  9/1999  Martinez ................ G06Q 10/20
                                                    715/764
8,917,513 B1 * 12/2014  Hazzard ............... H05K 5/0208
                                                    361/826

(Continued)

OTHER PUBLICATIONS

Piotrowski, Derek, "November—Work Progress Report: Personal Luck for Solo Miners, Night Theme, Ethereum Node Optimization", Dec. 2018, https://2miners.com/blog/november-work-progress-report-personal-luck-for-solo-miners-night-theme-ethereum-node-optimization/ (Year: 2018).*

(Continued)

*Primary Examiner* — James E Springer
(74) *Attorney, Agent, or Firm* — Fishman Stewart PLLC

(57) ABSTRACT

Systems and methods for reporting health status for a plurality of computing devices such as within a data center are disclosed. A management device connected to the computing devices via a network executes a management application that periodically requests and receives status data from the computing devices. A pool checker may be used to track corresponding pool status data, and an environment checker may periodically request and receive environmental data from environmental sensors for temperature, humidity, and audio. A report generator creates health reports and assigns device health classifications based on the device status data, the environmental data, and the pool health data. The data may be associated with one or more locations and customers, permitting filtering of the report.

19 Claims, 7 Drawing Sheets

(51) Int. Cl.
*G01K 3/00* (2006.01)
*G06F 11/30* (2006.01)
*H04L 43/06* (2022.01)

(52) U.S. Cl.
CPC .......... *G06F 11/0751* (2013.01); *G06F 11/30* (2013.01); *H04L 43/06* (2013.01)

(58) Field of Classification Search
USPC ........................................................ 340/500
See application file for complete search history.

(56) References Cited

U.S. PATENT DOCUMENTS

| | | | | |
|---|---|---|---|---|
| 9,886,338 | B1* | 2/2018 | Khokhar | G06F 11/34 |
| 10,691,528 | B1* | 6/2020 | Ferreira | G06F 11/0709 |
| 10,863,330 | B1* | 12/2020 | Lingle | H04W 4/38 |
| 11,070,452 | B1* | 7/2021 | Roy | H04L 43/20 |
| 2013/0128455 | A1* | 5/2013 | Koblenz | H05K 7/20836 |
| | | | | 165/294 |
| 2017/0126505 | A1* | 5/2017 | Cencini | H02H 7/20 |
| 2021/0027458 | A1* | 1/2021 | Chor | H04L 67/38 |

OTHER PUBLICATIONS

Minerstat, Features, May 24, 2019 https://web.archive.org/web/20190524024116/https://minerstat.com/features (Year: 2019).*

B.Top, What are the "Rejected Shares" in crypto mining?, Apr. 24, 2019, https://b-topmining.medium.com/what-are-the-rejected-shares-in-crypto-mining-b85978cb2abb#:~:text=So%20what%20are%20those%20Rejected%20Shares%3F&text=Rejected%20shares%20represent%20work%20that,on%20to%20the%20next%20block. (Year: 2019).*

Transcript with selected screenshots of "Firmware for ASIC S9. 20 Th/s." video posted to Youtube on Apr. 16, 2019; <https://wwwyoutube.com/watch?v=Sp_vg5_3IU4>; accessed Mar. 29, 2021.

Transcript with selected screenshots of "Vnish Smart Mine Antminer S9 Firmware Special Edition, Virus Blocking. Fee 1.7%-1.8%" video posted to Youtube May 21, 2019; <https://www.youtube.com/watch?v=Py9e7n73rtl>; accessed Mar. 29, 2021.

* cited by examiner

HEALTH REPORTING FOR COMPUTING DEVICES

CROSS-REFERENCE TO RELATED APPLICATIONS

This application claims priority to U.S. Provisional Patent Application Ser. No. 62/877,719, filed on Jul. 23, 2019, and titled "COMPUTING SYSTEM", the contents of which are hereby incorporated by reference in their entirety.

This application claims priority to U.S. Provisional Patent Application Ser. No. 62/877,740, filed on Jul. 23, 2019, and titled "COMPUTING SYSTEM", the contents of which are hereby incorporated by reference in their entirety.

TECHNICAL FIELD

The present disclosure generally relates to the field of computing and, more particularly, to systems and methods for managing a plurality of different computing devices.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Many cryptocurrencies (e.g., Bitcoin, Litecoin) are based on a technology called blockchain, in which transactions are combined into blocks. These blocks are stored with previous blocks of earlier transaction into a ledger (the "blockchain") and rendered immutable (i.e., practically unmodifiable) by including a hash. The hash is a number that is calculated based on the blocks and that meets the blockchain's particular criteria. Once the block and hash are confirmed by the cryptocurrency network, they are added to the blockchain. The hashes can be used to verify whether any of the prior transactions or blocks on the blockchain have been changed or tampered with. This creates an immutable ledger of transactions and allows the cryptocurrency network to guard against someone trying to double spend a digital coin.

Cryptocurrency networks generally consist of many participants that repeatedly attempt to be the first to calculate a hash meeting the blockchain network's requirements. They receive a reward (e.g., a coin reward or transaction fee reward) that motivates them to continue participating (mining).

Many blockchain networks require computationally difficult problems to be solved as part of the hash calculation. The difficult problem requires a solution that is a piece of data which is difficult (costly, time-consuming) to produce but easy for others to verify and which satisfies certain requirements. This is often called "proof of work". A proof of work (PoW) system (or protocol, or function) is a consensus mechanism. It deters denial of service attacks and other service abuses such as spam on a network by requiring some work from the service requester, usually meaning processing time by a computer.

While some participants in the networks may operate traditional computing devices such as PCs or servers, others operate specialized computing devices called mining rigs or miners. Because of the difficulty involved and the amount of computation required, the miners are typically configured with specialized components that improve the speed at which hashes or other calculations required for the blockchain network are performed. Examples of specialized components include application specific integrated circuits (ASICs), field programmable gate arrays (FPGA), graphics processing units (GPUs) and accelerated processing unit (APUs).

Computing devices in these networks are often run for long periods of time at high frequencies that generate large amounts of heat. Even with cooling (e.g., high speed fans), the heat and constant operations can negatively impact the reliability and longevity of the components in the miner. ASIC miners for example often have large numbers of hashing chips (e.g., 100's) that are more likely to fail as temperatures rise.

Many participants join mining pools to work collaboratively with other pool members on blockchain networks. Some participants operate large numbers (e.g., 100's, 1000's or more) of computing devices of different types (e.g., different generations of miners from one manufacturer or different generations from different manufacturers) concurrently in large data centers which provide power, network and management services. However, managing these large numbers of computing devices can be difficult, particularly as they age and start to require repairs. Examples of repairs they may require include simple operations such as resetting or rebooting, to cleaning off collected dust that impedes proper cooling, to replacing failing memory, processing boards, ASIC chips, power supplies, or fans (e.g., with worn out bearings).

For computing devices working on compute-intensive tasks such as cryptocurrency mining, there is even more pressure on data center staff to identify problems quickly and prevent them where possible. A computing device that is not performing optimally in cryptocurrency mining can result in a financial loss to the owner of the device. For example, if the device is consuming energy but not computing at full efficiency, the owner of the device may spend more in electricity than the computing device earns in cryptocurrency. Also, once a device ceases contributing to the network no revenue is being derived from that computing device. Since these computing devices continually and rapidly depreciate over time whether they are running or not, there is significant pressure on data center staff to keep each computing device's uptime as high as possible. Furthermore, once a device completely fails, it may take more time to determine the original root cause of the problem.

Current management solutions provide only limited functionality to support data center staff in this context. While prior solutions may properly identify failed devices, they do not provide data center staff with the tools to easily identify those devices before failure that are more likely to benefit from preventative maintenance. For at least these reasons, there is a desire for an improved solution for managing large numbers of computing devices.

SUMMARY

A system and method for generating health reports for computing devices is contemplated. The health reports are automatically updated periodically and allow data center staff to more easily determine which computing devices are having health issues and should be considered for preventative maintenance. This makes managing large numbers of computing devices such as miners (e.g., traditional CPU-based devices as well as ASIC, GPU, and FPGA devices) easier. The computing devices may be different models and from different manufacturers.

In one embodiment, the method may comprise periodically requesting device status data from one or more of the computing devices, pool status data from a pool (e.g., mining pool or other distributed computing pool) to which the devices are contributing, and environmental status data from one or more environmental sensors. Status data responses are received from the computing devices, the pool, and the environmental sensors, and a health report is created based on the received status data responses. The health report comprises a summary of helpful information for data center staff and owners of the computing devices, such as computing device error information based on the device status data, environmental health information based on the environmental status data, pool health information based on the pool status data. It may also include luck information based on the pool status data. In this context, luck represents tracking which computing devices have been successful in winning a block (i.e., being the first to solve a block). In mining cryptocurrency in pools, luck is of interest as the miner that first solves the block may be awarded a bonus by the mining pool.

The environmental sensors may for example include temperature and or humidity sensors. In response to receiving data from these sensors outside a predefined safe range, temperature or humidity warnings may be generated. As the computing devices are typically positioned on racks in the data center to intake air from a cool aisle and exhaust air to a hot aisle, the environmental sensors may be positioned to measure the temperature and humidity at the hot aisle and cold aisles, as well as the temperature/humidity at the device itself. The environmental status data received may be associated with one or more of the computing devices based on the proximity of the location of the computing device to the environmental sensors. This may enable data center staff to determine areas of the data center with suboptimal cooling (e.g. a partially clogged ventilation shaft).

In some embodiments, the environmental sensors may comprise one or more microphones positioned to periodically capture real-time audio signals from the computing devices. These can be compared with a previously recorded baseline known good audio signal representative of the computing devices operating in a known good state. The health report may include a warning for one or more devices near the microphone(s) in response to the signal difference being outside a predefined safe audio range (e.g., a high pitch noise indicating the wearing out of a device's fan's bearings).

Different subsets of the computing devices may be assigned to participate in different pools (e.g., a quarter of the devices may be mining for pool A, another quarter may be mining for pool B, etc.). Pool status data received from one or more pools may be associated with the computing devices (and their location in the data center) that are contributing work to the pool originating the data. This pool status data may for example include data regarding accepted shares, difficulty, and solved blocks. Similarly, the received device status data (e.g., hash rate) may be associated with the device originating the received device status data and that device's location as well.

Associating device location information with the status data may for example permit data center staff to more easily determine that devices in a particular rack are reporting more errors than others or not contributing as much to their pool as other devices. This helpful information may allow the data center staff to troubleshoot that rack (e.g., check air flow for the rack, the network switch for the rack, or the power distribution unit feeding power to that rack). The health report may be presented via a web page or other user interface that comprises controls permitting a user such as a data center technician (DCT) or customer (e.g., owner or administrator of the computing device) to filter the health report based on location (e.g., a particular data center, or rack within a data center), customer, or device type (e.g., by age, manufacturer, model).

This status information for each of the computing devices may be incorporated into the health report, both individually and in aggregated form. For example, a plurality of status data (e.g., health signals), which may be individually unreliable (e.g., the is network down, or a computing device is temporarily non-responsive, etc.), may be combined (e.g. triangulated) in order to classify a computing device into a predicted health state/classification. For example, out of safe range environmental data may be combined with other data (e.g., device errors captured, pool data, etc.) into an overall health classification for each device (e.g., optimal, sub-optimal, degraded, repeat offender). Health status data may also be combined across devices to provide helpful information such as a particular customer's device health status category distribution (e.g. for customer X, 90% of devices are in optimal health, 12% sub-optimal, etc.).

A system for managing networked computing devices is also contemplated. In one embodiment, the system may for example comprise a management application executing on a management device connected to the computing devices via the network. The management application may for example be stored as instructions on a computer-readable storage medium (e.g., a hard drive, SSD, or flash memory device) and be executed by the management device. The management application may comprise (i) a device status checker that periodically requests and receives status information from the computing devices, (ii) an environment checker that periodically requests and receives environmental information from one or more environmental sensors (e.g., temperature, humidity, audio) within the data center, and (iii) a report generator that creates health reports based on the received status information and received environmental information. The health report may include one or more of the following: computing device error data, environmental health data, pool health data, and luck data. The management application may also include a pool checker that periodically requests and receives pool performance information from one or more pools associated with the computing devices, and the pool performance information may be included the health reports.

The health reports may include both raw data (e.g., table view or graph view), and higher level views (e.g. a graphical depiction of each rack of the data center with toggleable color-coded indicators for overall device health (combining all the status data), device status (e.g., device-specific errors) environmental health, and pool status.

The management application may also include a luck checker that tracks luck information for each of the computing devices, such as the number of blocks solved by the device (the more blocks, the luckier the device is), and the report generator may incorporate the luck information into the health reports. Luck information may be helpful to data center staff and customers to explain differences in revenue generated over time by different subsets of computing devices (e.g., the difference may not be due to device malfunction, but may merely be due to random luck).

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they do not limit the present disclosure to these embodiments and/or examples. On the contrary, the present disclosure covers alternatives, modifications, and equivalents.

Various embodiments are described herein for various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Figure 1:
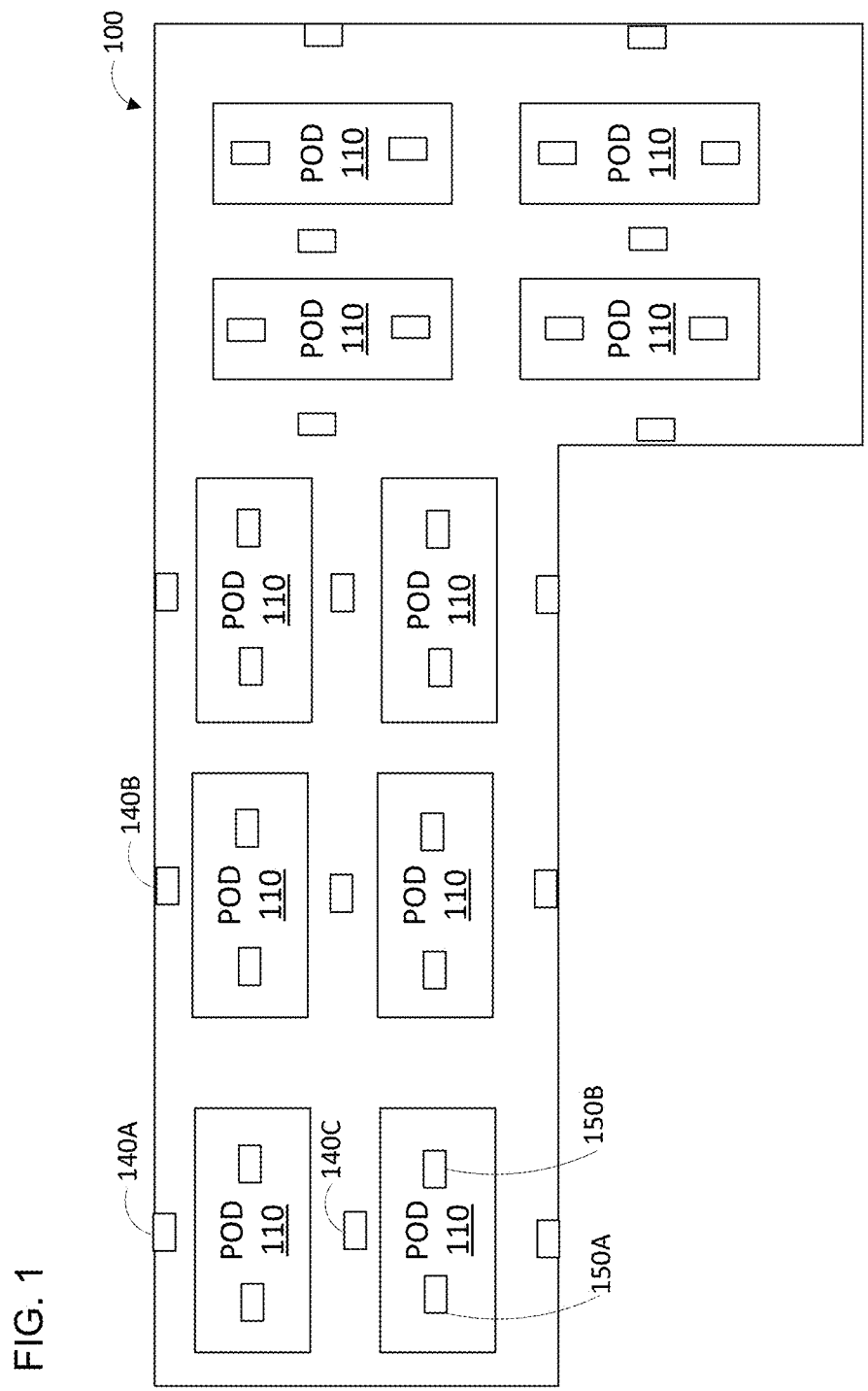
FIG. 1 is a top-down view of one example of a data center for computing devices.

Referring now to FIG. 1, a top-down view of one example of a data center 100 for computing devices is shown. The data center 100 is configured with a large number of pods 110. Pods are standardized blocks of racks, either in a row or (more typically) a pair of rows, that share some common infrastructure elements like power distribution units, network routers/switches, containment systems, and air handlers. For example, a pod may have two parallel racks of devices, spaced apart and each facing outwards. The devices on the racks may all be oriented to pull cool air in from outside the pod and discharge the hot air (heated by the computing devices) into the empty space in the center of the pod where the hot air then rises up and out of the data center. For example, there may be hot air ducts positioned above the middle of each pod to capture the hot waste air and then discharge it out of the data center via vents in the roof of the data center. Data center 100 may also include environmental sensors such as sensors 140A-C and 150A-B. These sensors may be networked and provide environmental information such as temperature, humidity, air pressure, and real-time or near real-time audio. Some sensors may be in cold aisle sections of data center 100, such as sensors 140A-C, and others may be positioned inside hot aisle portions of data center 110, such as sensors 150A and 150B.

Figure 2:
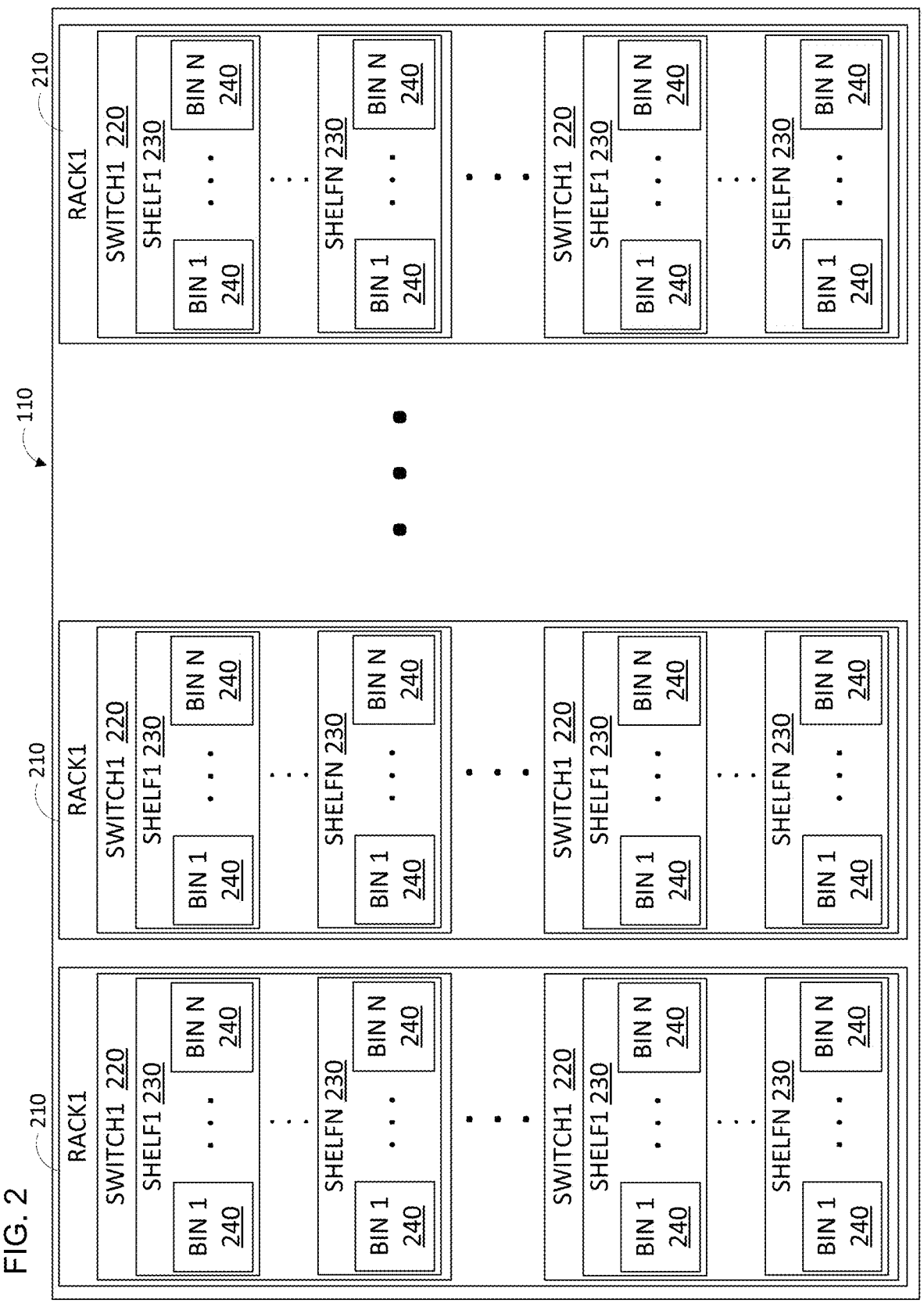
FIG. 2 is a front view of one example of a pod in a data center for computing devices.

Turning now to FIG. 2, the front side of one example of a pod 110 is shown. The pod 110 has a number of racks 210 that each have a number of shelves 230 for holding computing devices. For organization and management purposes, the shelves may be grouped together in switch sections 220 that are each supported by the same network switch. In each of the shelves 230 there may be multiple bin locations 240 that each hold a single computing device. Each computing device may be installed in a bin (e.g., a location or tray or slot) with connections for power and a network connection.

Figure 3:
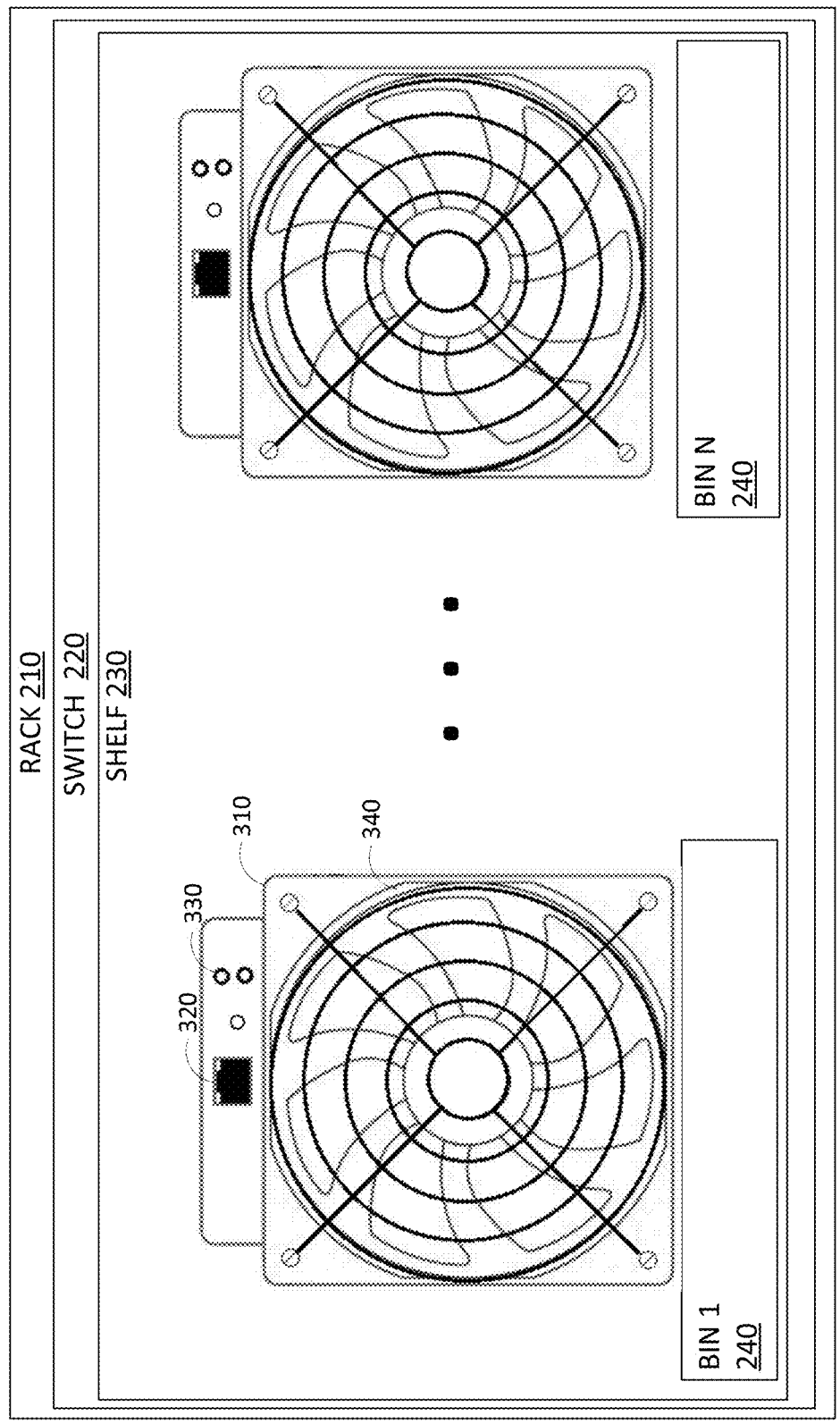
FIG. 3 is an illustration of one example of a portion of a rack for computing devices in a data center.

Turning now to FIG. 3, a more detailed frontal view of one shelf 230 in an example rack 210 is shown. In this example, a computing device 310 is installed in each bin 240 in the shelf 230. In this example, computing device 310 is an ASIC miner, but other computing device types are possible and contemplated. ASIC miners typically include one or more cooling fans 340 that draw air through the center of the miner where there are multiple hash boards performing calculations and generating heat. Other types of computing devices are possible and contemplated, including GPU and FPGA miners, as well as more traditional personal computers and servers. The location of a computing device (e.g. within the data center) may be tracked for example by pod, rack, shelf, bin or by the network switch and port to which the device is connected (the port may then be mapped to a specific shelf or location).

Figure 4:
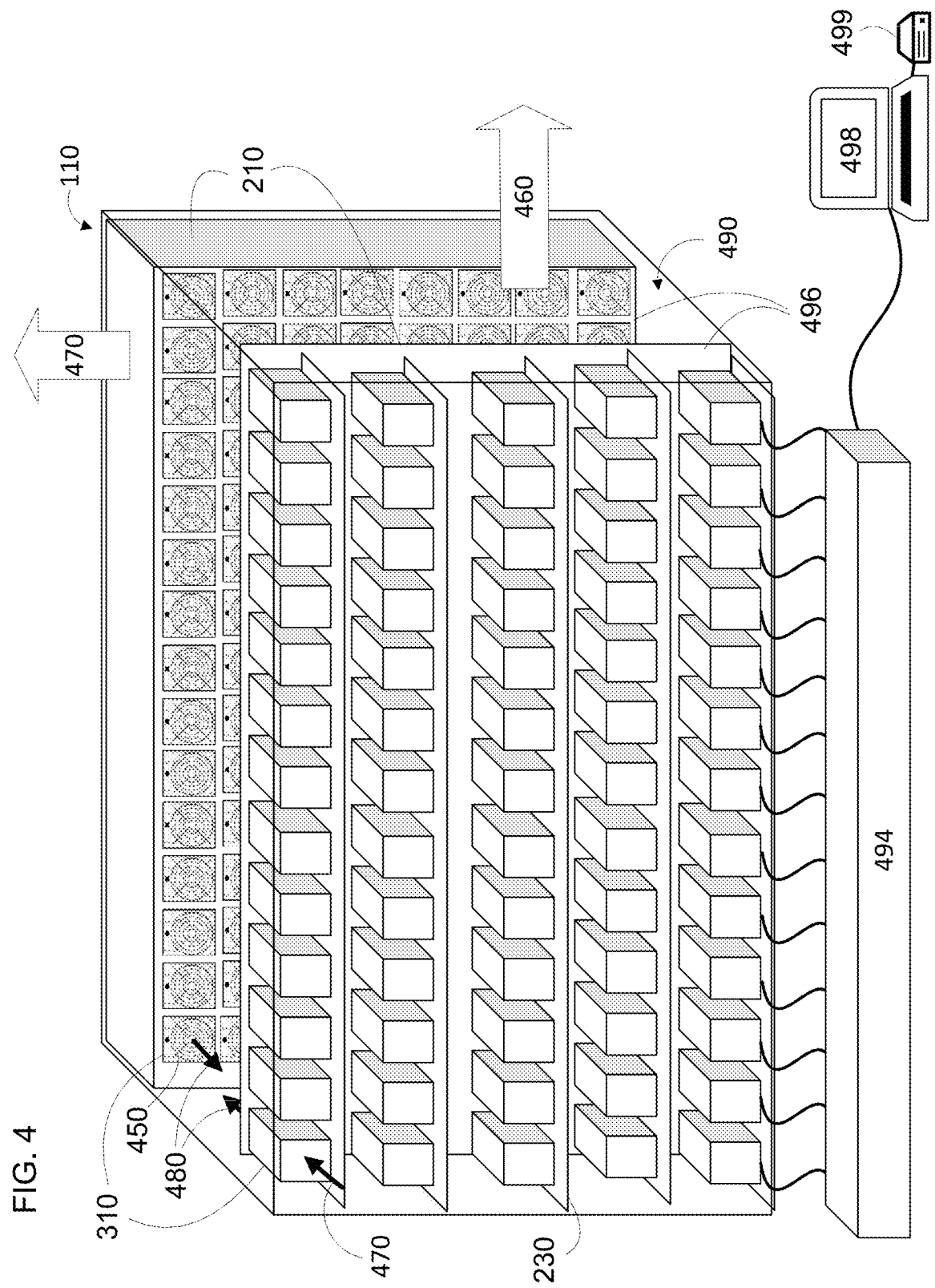
FIG. 4 is a perspective view of one example embodiment of a pod housing computing devices in a data center.

Turning now to FIG. 4, a perspective view of one example of a pod 110 is shown. This example of pod 110 has racks 210 that each have a number of shelves 230 for holding computing devices 310, thereby creating a two-dimensional array of computing devices on each rack or group of racks. In some embodiments, racks 210 may have rails that hold computing devices 310 in place on shelves 230. In other embodiments, computing devices 310 may be simply placed on shelves 230 or positioned in trays on shelves 230. Each computing device 310 has one or more cooling fans 450 configured to draw air from outside the pod (e.g., from the cool aisle) into the computing device for cooling, as shown by arrow 470. The moving air draws heat out from computing device 310 and is exhausted from the computing device as shown by arrows 480.

In some embodiments, computing devices 310 may have two fans, one on the intake side and one on the exhaust side. Heated air is exhausted by computing devices 310 into the space 490 between racks 210, which is often called a hot aisle. The space between racks 210 is typically sealed except for one or more exhaust openings through which the heated air exits. In some embodiments, these openings may be at the side, with heated air exiting as indicated by arrow 460. In other embodiments, these exhaust openings may be located at the top of hot aisle 490 with the heated air exiting above the pod as indicated by arrow 470. In some embodiments, computing devices 310 are positioned adjacent to an air barrier 496 with openings large enough to allow the heated exhaust air from each computing device 310 to pass into hot aisle 490 but not escape out of hot aisle 490 other than through the exhaust vents.

Computing devices 310 are networked together with network switches. One example switch 494 is shown, but many switches are typically used in a data center. Computing devices 310 may be organized by mapping physical computing device positions (e.g., bins) within the pod, rack and shelf by the network ports on switch 494. This network connection allows management instructions and computing jobs to be sent to each computing device 310, and data such as device status information (e.g., temperature information) and results of the computing jobs to be returned. Switch 494 may also be connected to other networks such as the internet, as well as a management device 498 that is configured to execute a management application (e.g. stored on computer readable media 499) to manage computing devices 310. Management device 498 may be a traditional PC or server, or specialized appliance. Management device 498 may be configured with one or more processors, volatile memory, and non-volatile memory such as flash storage or internal or external hard disk (e.g., network attached storage). The management application or module is preferably implemented in software (e.g., instructions stored on a non-volatile storage medium such as a hard disk, flash drive, or DVD-ROM), but hardware implementations are possible. Software implementations of the management application may be written in one or more programming languages or combinations thereof, including low-level or high-level languages, with examples including Java, Ruby, JavaScript, Python, C, C++, or C#. The program code may execute entirely on the management device 498 as a stand-alone software package, partly on the management device 498 and partly on a remote computer or computing devices 310, or entirely on a remote computer or computing devices 310.

In order to better manage computing devices 310, the management application may be configured to dispatch instructions to computing devices 310 to request device status information, e.g., fan speed, device temperature, rate of work completion (e.g. hash rate), processor voltage, processor frequency, memory voltage, memory frequency.

Figure 5:
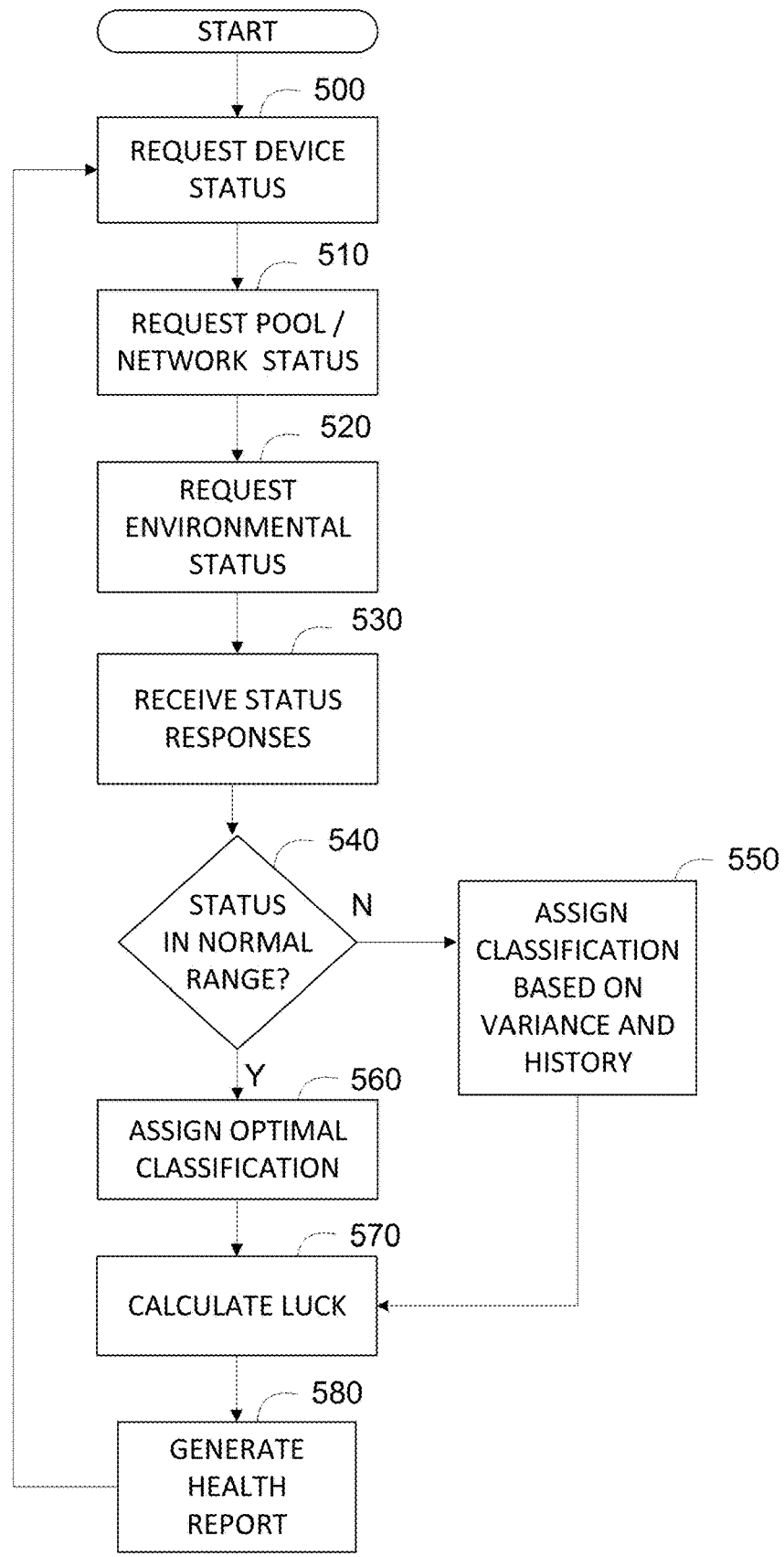
FIG. 5 is a flowchart illustrating an example embodiment of a method for managing a plurality of computing devices according to teachings of the present disclosure.

Turning now to FIG. 5, a flowchart representing one example embodiment of a method for managing a number of computing devices is shown. Device status may be requested (step 500) by periodically sending a request to each computing device. Device status requests may for example include requesting hash rate information for each computing device, and a list of errors experienced by the device (e.g., since the last status request). Some devices (e.g., ASIC-based miners) may have large numbers of processing integrated circuits (ICs) on multiple boards, and some ICs may fail without bringing down the whole computing device. A list of failed ICs may be included in the list of errors experienced by the device.

Network and pool status may also be requested (step 510). Network and pool status may be requested from a server or servers operating the pool and may include the number of shares accepted, shares rejected, and blocks solved. Environmental status may be requested (step 520), which may include temperature data, humidity data, and sound data from one or more environmental sensors near the computing devices. If the valid responses to the status requests are received from a device and the associated sensors and pools, and all the responses are all within a predetermined normal range (step 540), then the device may be assigned an optimal classification (step 560). If not, another classification may be assigned (step 550), such as sub-optimal (e.g., one status is moderately out of normal range), degraded (e.g., multiple statuses are significantly out of normal range), or repeat offender (e.g., a device having more than a predetermined number of errors or out of normal range statuses within a certain timeframe). A luck value may also be determined (step 570) for each device (e.g., based on the number of blocks solved, which may be provided by the pool). A health report may be generated (step 580) and stored in a database for presentation to the user upon request (e.g., via a filterable user interface).

Figure 6:
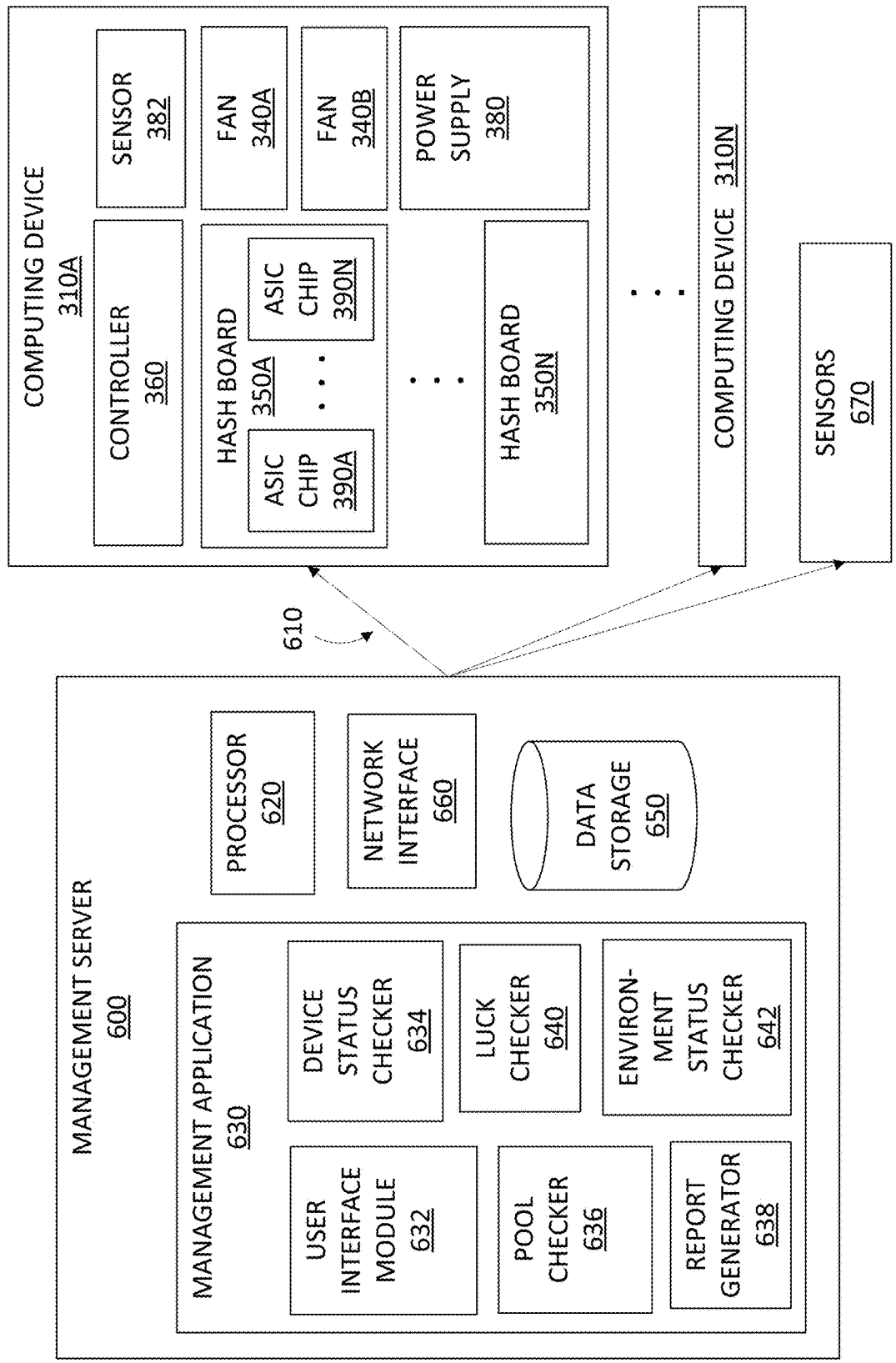
FIG. 6 is an illustration of an example embodiment of a system for managing computing devices in a data center according to the teachings of the present disclosure.

Turning now to FIG. 6, an illustration of an example embodiment of a system for managing computing devices in a data center is shown. In this embodiment, the system comprises a number of computing devices 310A-N (e.g., miners). The computing devices 310 communicate over a network 610 with a management server 600 via the server's network interface 610. While wireless networks are possible, current computing device density in data centers means wired networks such as wired Ethernet may be preferred for communications between management server 600 and computing devices 310.

In some embodiments, computing devices 310 may include a controller 360 and a network interface for communicating with management server 600 via network 610. Controller 360 may be configured to send compute tasks to one or more compute or hash boards 350, each having a number of GPU or ASIC chips 390 that can operate at a frequency specified by the controller. Controller 360 may also be configured to receive requests for device status from management application 630 via network 610 and respond thereto. Computing device 310 may further comprise multiple cooling fans 340A-B and one or more power supplies 380. In some embodiments, the voltage output by the power supply to ASIC chips 390 may be varied based on settings configured by controller 360. Higher voltage and frequency levels for ASIC chips 390 will increase performance, but they may also increase heat and negatively impact longevity. Knowing the health status of each computing device 310 may permit the data center staff to better optimize these settings for each computing device. Computing devices 310 may be configured with one or more sensors 382 that controller 360 can use to provide status data to management application 630. In one embodiment, these may comprise temperature sensors, but other sensor types such as humidity sensors and microphones may also be used.

Management server 600 may be a traditional PC or server, or specialized appliance. Management server 600 may be configured with one or more processors 620, volatile memory and non-volatile memory such as flash storage or internal or external hard disk (e.g., network attached storage accessible to server 600). Management server 600 is configured to execute management application 630 to assist users (e.g., data center staff and customers) with managing computing devices 310. Management server 600 may be located within the same data center or facility as computing devices 310 or located remotely and connected to computing devices 310 via the Internet or other wide area network.

Management application 630 is preferably implemented in software (e.g., instructions stored on a non-volatile storage medium such as a hard disk, flash drive, or DVD-ROM), but hardware implementations are possible. Management application 630 may include a number of modules, including for example, a user interface module 632 that displays data to a user and receives input from a user (e.g., via an external display or via the user's web browser), a device status checker 634 that sends status queries to get status data for computing devices 310 (e.g., periodically polling for each device's status including hash rate, errors, fan speed, voltage level, operating frequency, etc.), a pool checker 636 that communicates with one or more pools (e.g., cryptocurrency mining pools, computation pools) and receives pool health/status information back (e.g., accepted shares, difficulty, rejected shares, etc.), an environment status checker 642 that communicates with one or more environmental sensors 670 via network 610 to gather environmental status data (e.g., temperature, humidity, audio). In some embodiments, management application 630 may also comprise a luck checker 640 that tracks blocks found by each computing device.

Management application 630 may further comprise a health report generator 638 that stores the status data received by the checkers (e.g., in a database such as data storage 650). In some embodiments, the status data may be stored along with date, time, location, and device ids corresponding to the data. For example, temperature data received from a cold aisle temperature sensor may be associated with the date and time that the temperature was taken, along with the devices that are located in close proximity to the sensor (e.g. devices in the rack nearest the sensor). The report generator 638 may store the status data in data storage 650 individually and in aggregate (e.g., by combining status date to generate health classifications for individual computing devices and groups of computing devices). The health report generator 638 may compare the received status data with defined normal ranges. Any status data that is outside these normal ranges may be flagged and warnings may be generated. Status data outside the normal ranges may also cause report generator 638 to change the health classification of the impacted computing devices. In some embodiments, the user interface module 632 may be configured to provide an interface so that users may view the health report information in a web or app page in one or more filterable views.

Figure 7:
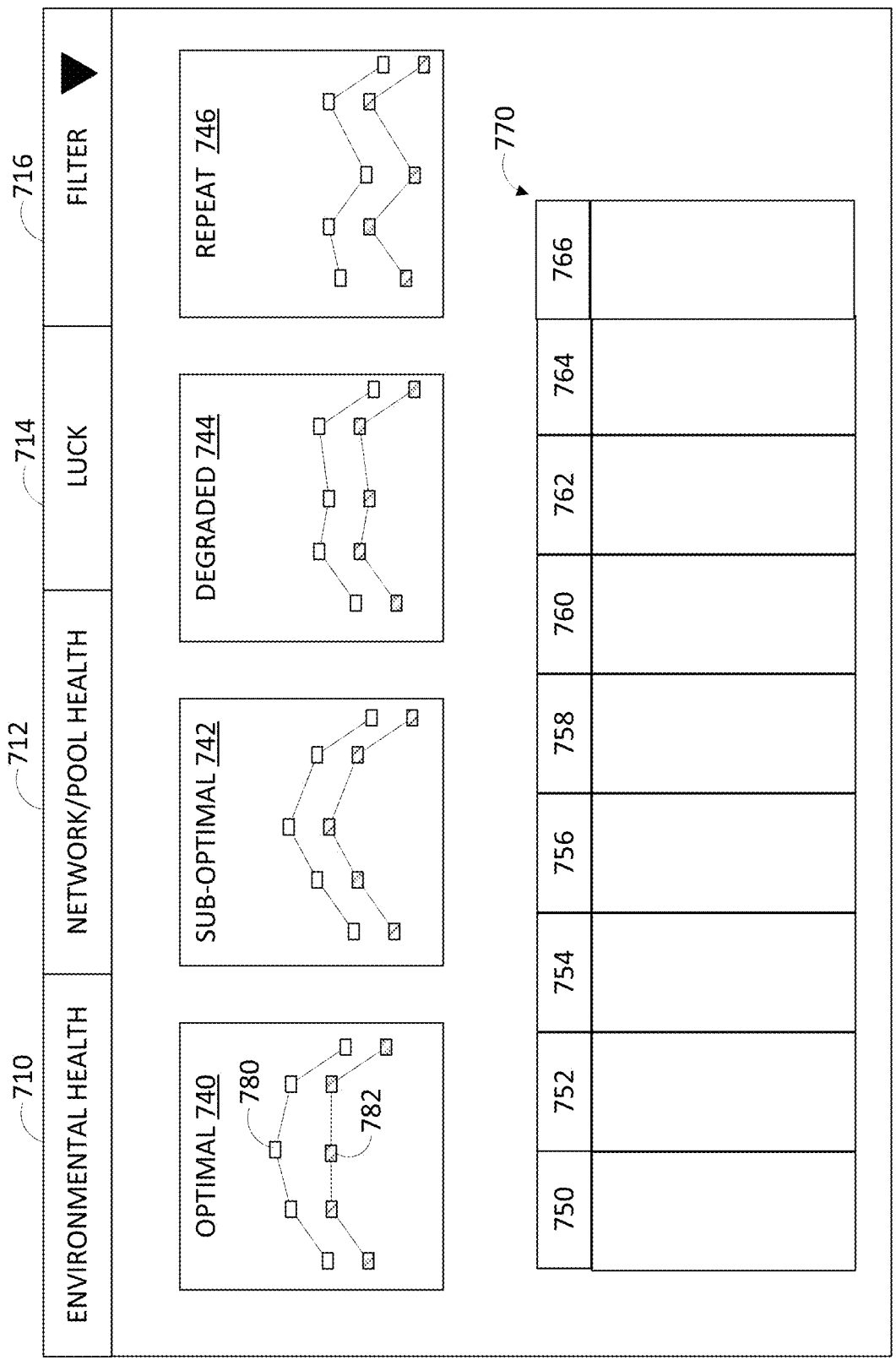
FIG. 7 is an illustration of one example embodiment of a user interface displaying a page of an example health report according to teachings of the present disclosure.

Turning now to FIG. 7, an illustration of an example of one such page displaying an example health report 700 is shown. In this example, the page comprises a series of tabs 712-716 providing access to different sets of information and visualizations of the health status information in health report 700, including for example environmental health tab 710, network/pool health tab 712, and luck tab 714. In one embodiment, the data in graphs 740-760 and table 770 may change according to the selected tab. Dropdown filter control 716 may present the user with additional options for filtering the health status report information within a view selected by the tab. For example, control 716 may permit the user to select a time, date, or date range for which the health status information should be displayed. Control 716 may also permit the user to filter the health status information based on location (e.g., for a particular data center, pod, rack, switch), device type (e.g., manufacturer, model, age), pool, account or customer. Access to filtering by customer may be limited to data center staff, as security concerns may prohibit customers from viewing other customers' data.

For example, when the environmental health tab 710 is selected, graph 740 may display a graph of the number of devices in optimal environmental health (e.g., with all associated environmental status data in normal range), graph 742 may display a graph of the number of devices in sub-optimal environmental health (e.g., with some environmental status data outside normal range), graph 744 may display a graph of the number of devices in a degraded state (e.g., with one or more errors or environmental health status data significantly outside the normal range), and graph 746 may display a graph of the number of devices that are repeat offenders (e.g., with multiple repeated errors or repeated environmental status data significantly outside normal range over a predefined time period).

One example of suboptimal health may be a computing device that has a higher rejected share percentage (e.g. above 2%) from the pool for which it is working. Higher rejected shares (e.g., the device was too slow to respond with the share and the pool had already moved to another block) may result from a number of factors, including for example: (i) the computing devices running too hot due to fan settings or malfunction causing insufficient cooling/airflow, (ii) network connectivity issues with the pool, (iii) high levels of dust inside the computing device impacting cooling; (iv) hardware issues in the computing devices (e.g. a failing power supply), (v) bad settings on the device (overclocking/underclocking or bad pool configuration), and (vi) pool problems such as an overloaded pool server.

Providing this health information may indicate to the data center staff that there is a network or pool issue that should be investigated. Graphs 740-746 may be presented in a number of different ways, for example the number of devices may be the vertical axis versus the machine type on the horizontal axis. Other graph configurations are possible and contemplated based on the selected filter (e.g., the number of devices versus device age, number of devices versus pool being mined, number of devices versus rack, number of devices versus switch, number of devices versus pod, etc.). Multiple graph lines or data sets may be displayed in each graph 740-746. For example, graph line 780 may plot last week's data while graph line 782 may plot this week's data. Other combinations of plots are possible and contemplated (e.g. separate graph lines for devices and hash boards, each graph line representing a different customer, each graph line representing different generations of devices, etc.). Other graph types such as bar charts are also possible and contemplated, and visual alerts such as color coding may be used to highlight problematic data for users.

The health status data may also be presented in table view 770 in addition to or in place of graph views 740-746. In one example embodiment, each row represents a particular device type and column 750 is the machine type, column 752 is the number of devices, column 754 is the cold aisle average temperature, column 756 is the hot aisle average temperature, column 758 is the number of hardware errors, column 760 is the number of devices of the row's device type in an optimal state, column 762 is the number of devices of the row's device type in a suboptimal state, column 764 is the number of devices of the row's device type in a degraded state, and column 766 is the number of devices of the row's device type that are classified as repeat offenders. In one embodiment, based on filtering selections in control 716, the rows may be changed from device type to other classifications (e.g., by pod, rack, switch) to permit data center staff to better determine where problems may be (e.g., by seeing that a particular pod or rack is experiencing more problems than others).

Reference throughout the specification to "various embodiments," "with embodiments," "in embodiments," or "an embodiment," or the like, means that a particular feature, structure, or characteristic described in connection with the embodiment is included in at least one embodiment. Thus, appearances of the phrases "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such elements. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of "and" and "or" are to be construed broadly (e.g., to be treated as "and/or"). For example, and without limitation, uses of "and" do not necessarily require all elements or features listed, and uses of "or" are inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

All matter contained in the above description or shown in the accompanying drawings shall be interpreted as illustrative only and not limiting. Changes in detail or structure may be made without departing from the present disclosure.

It should be understood that a computer, a system, and/or a processor as described herein may include a conventional processing apparatus known in the art, which may be capable of executing preprogrammed instructions stored in an associated memory, all performing in accordance with the functionality described herein. To the extent that the methods described herein are embodied in software, the resulting software can be stored in an associated memory and can also constitute means for performing such methods. Such a system or processor may further be of the type having ROM, RAM, RAM and ROM, and/or a combination of non-volatile and volatile memory so that any software may be stored and yet allow storage and processing of dynamically produced data and/or signals.

It should be further understood that an article of manufacture in accordance with this disclosure may include a non-transitory computer-readable storage medium having a computer program encoded thereon for implementing logic and other functionality described herein. The computer program may include code to perform one or more of the methods disclosed herein. Such embodiments may be configured to execute via one or more processors, such as multiple processors that are integrated into a single system or are distributed over and connected through a communications network, and the communications network may be wired and/or wireless. Code for implementing one or more of the features described in connection with one or more embodiments may, when executed by a processor, cause a plurality of transistors to change from a first state to a second state. A specific pattern of change (e.g., which transistors change state and which transistors do not), may be dictated, at least partially, by the logic and/or code.

What is claimed is:

1. A method for reporting health of a plurality of computing devices, the method comprising:
periodically requesting device status data from one or more of the computing devices;
periodically requesting pool status data from a pool to which at least a subset of the computing devices are contributing work;
periodically requesting environmental status data from one or more environmental sensors;
receiving status data responses from the computing devices, the pool, and the one or more environmental sensors;
calculating a health status classification for each computing device based on the received status responses; and
creating a health report including the health status classifications, device error information based on the device status data, environmental health information based on the environmental status data, pool health information based on the pool status data, and luck information based on the pool status data; and
wherein calculating the health status classification for each computing device includes assigning a computing device:
an optimal classification if all of the received status responses are within a predetermined normal range;
a degraded classification if a plurality of the received status responses are out of the predetermined normal range; and
a repeat offender classification if (i) one or more of the received status responses is out of the predetermined normal range more than a predetermined number of times within a predetermined timeframe and/or (ii) the device status data indicates that more than a predetermined number of errors has occurred.

2. The method of claim 1, wherein the device status data includes a computing device's hash rate, error list, fan speed, processor voltage, processor frequency, memory voltage, and memory operating frequency.

3. The method of claim 1, wherein the pool status data includes a number of shares accepted, a number of shares rejected, a number of blocks solved, and difficulty.

4. The method of claim 1, wherein the environmental sensors comprise temperature sensors, and wherein the environmental status data comprises temperature data, the method further comprising:
comparing temperature data from the temperature sensors to a predefined safe temperature range; and
adjusting the health classifications for computing devices associated with out of safe temperature range temperature data.

5. The method of claim 1, wherein the environmental sensors comprise humidity sensors, and wherein the environmental status data comprises humidity data, method further comprising:
comparing humidity data from the humidity sensors to a predefined safe humidity range; and
adjusting the health classifications for computing devices associated with out of safe humidity range humidity data.

6. The method of claim 1, wherein the environmental sensors comprise one or more microphones, and wherein the method further comprises:
capturing from the microphones a baseline known good audio signal representative of at least a subset of the computing devices operating in a known good state; and
periodically capturing real-time audio signals from the microphones; and comparing the real-time audio signals with the baseline known good audio signal to determine a signal difference; and adjusting the health classifications for computing devices associated with audio signals having a signal difference outside a predefined safe range.

7. The method of claim 1, further comprising:

associating the received environmental status data with one or more of the computing devices based on the proximity of the location of the computing device to the environmental sensors;

associating the received pool status data with one or more of the computing devices contributing work to the pool originating the received pool status data; and associating the received device status data with the device originating the received device status data.

8. The method of claim 6, wherein:

the pool status data comprises a number of accepted shares and difficulty; and the device status data comprises a hash rate of the computing device.

9. The method of claim 7, wherein the health report is a presented via a page comprising controls permitting a user to filter the health report based on one or more locations.

10. A system for managing a plurality of networked computing devices in one or more data centers, the system comprising:

a management application executing on a management device connected to the plurality of networked computing devices, wherein the management application comprises:

a device status checker that periodically requests and receives status information from the computing devices, an environment checker that periodically requests and receives environmental information from one or more environmental sensors within the data center, and a report generator that calculates a health status classification for each computing device and creates a health report based on the received status information and received environmental information;

wherein the environmental sensors further comprise one or more microphones positioned to capture sound from the computing devices;

wherein the environment checker is configured to:
(i) periodically capture real-time audio signals from the microphones,
(ii) compare them with a known good baseline audio signal representative of normal operation of the computing devices, and
(iii) generate a warning when the difference is outside an expected range, wherein the report generator is configured to incorporate the warning into the health reports and health status classifications.

11. The system of claim 10, further comprising a pool checker that periodically requests and receives pool performance information from one or more pools associated with the computing devices, wherein the report generator incorporates the pool performance information into the health reports and health status classifications.

12. The system of claim 10, wherein the computing devices are positioned in the one or more data centers to intake air from a cool aisle and exhaust air to a hot aisle, wherein the environmental sensors comprise at least one of:

temperature sensors positioned to measure hot aisle and cold aisle temperatures; and humidity sensors positioned to measure hot aisle and cold aisle humidity.

13. The system of claim 10, wherein the management application further comprises a luck checker, wherein the luck checker tracks luck information for each of the computing devices, wherein the luck information comprises a number of blocks solved, wherein the report generator incorporates the luck information into the health reports.

14. A non-transitory, computer-readable storage medium storing instructions executable by a processor of a computational device, which when executed cause the computational device to:

periodically request device health status data from one or more of a plurality of computing devices connected via a network;

periodically request pool health status data from a computing pool associated with at least a subset of the plurality of computing devices;

periodically request environmental health status data from one or more environmental sensors;

receive responses from the computing devices, the computing pool, and the one or more environmental sensors;

calculate health classifications for the computing devices based on the responses;

create a health report based on the received responses, wherein the health report comprises alerts for out of normal range computing device health status data, environmental health status data, and pool health status data; and assign a computing device:
an optimal classification if all of the received responses are within a predetermined normal range;
a degraded classification if a plurality of the received responses are out of the predetermined normal range; and
a repeat offender classification if (i) one or more of the received responses is out of the predetermined normal range more than a predetermined number of times within a predetermined timeframe and/or (ii) the device health status data indicates that more than a predetermined number of errors has occurred;

wherein the pool health status data includes a number of shares rejected.

15. The medium of claim 14, further comprising instructions which when executed cause the computational device to periodically request and receive pool performance information from one or more pools associated with the computing devices, wherein the health report incorporates the pool performance information.

16. The medium of claim 15, further comprising instructions which when executed cause the computational device to track luck information for each of the computing devices, wherein the luck information comprises a number of blocks solved, wherein the health report incorporates the luck information.

17. The medium of claim 15, wherein the environmental sensors comprise temperature sensors, wherein the health report incorporates temperature information from the temperature sensors.

18. The medium of claim 15, further comprising instructions which when executed cause the computational device to associate location information with the environmental health status data.

19. The medium of claim 14, further comprising instructions which when executed cause the computational device to:

periodically capture real-time audio signals from one or more microphones positioned to capture sound from the computing devices, compare the captured real-time audio signals with a known good baseline audio signal representative of normal operation of the computing devices, and generate a warning when a difference between the captured real-time audio signals and the baseline audio signal is outside an expected range.

* * * * *